United States Patent [19]

Yoakum et al.

[11] Patent Number: 4,608,339
[45] Date of Patent: Aug. 26, 1986

[54] PROTOPLAST FUSION METHOD FOR HIGH-FREQUENCY DNA TRANSFECTION IN HUMAN CELLS

[76] Inventors: George H. Yoakum, 10244 Millstream Dr., Gaithersburg, Md. 20879; Curtis C. Harris, 8402 Thornden Ter., Bethesda, Md. 20817; Brent E. Korba, 8255 Stone Trail Ct., Laurel, Md. 20707; John F. Lechner, 12908 Neola Rd., Wheaton, Md. 20906

[21] Appl. No.: 545,257

[22] Filed: Oct. 25, 1983

[51] Int. Cl.⁴ .................. C12N 15/00; C12N 5/00; C12P 21/02
[52] U.S. Cl. .................. 435/172.2; 435/240; 435/70; 935/93; 935/57; 935/65; 935/71; 935/73; 935/29; 935/12
[58] Field of Search .................. 435/68, 172.2, 172.3, 435/91, 240; 935/12, 29, 32, 54, 57, 65, 73, 71, 93

[56] References Cited

FOREIGN PATENT DOCUMENTS 0043075  1/1982  European Pat. Off. .............. 935/28

OTHER PUBLICATIONS

Mercer, "Techniques for Decreasing the Toxicity of Polyethylene Glycol", Techniques in Somatic Cell Genetics, ed. Shay, pp. 23–34 (1982).
Sandri-Goldin et al, "High Efficiency Transfer of DNA into Eukaryotic Cells by Protoplast Fusion", Methods in Enzymology, 101, pp. 402–411 (1983).
Sandri-Goldin et al, "High Frequency Transfer of Cloned Herpes Simplex Virus Type I Sequences to Mammalian Cells . . . ", Molecular and Cellular Biology 1(8), pp. 743–752 (1981).
Schaffner, "Direct Transfer of Cloned Genes from Bacteria to Mammalian Cells," Proceedings of the National Academy of Sciences, 77(4) pp. 2163–2167 (1980).
Rassoulzadegan et al, "High Frequency of Gene Transfer after Fusion Between Bacteria and Eukaryotic Cells", Nature, 295, pp. 257–259 (1982).
Stahl et al, "Hepatitis B Virus Core Antigen: Synthesis in *Escherichia coli* and Application in Diagnosis", Proceedings of the National Academy of Sciences, 79, pp. 1606–1610 (1982).
Gough et al, "Expression of Hepatitis B Virus Surface, Core and E Antigen Genes by Stable Rat and Mouse Cell Lines", Journal of Molecular Biology, 162, pp. 43–67 (1982).
Mulligan et al, "Expression of a Bacterial Gene in Mammalian Cells", Science, 209, pp. 1422–1427 (1980).
Gough, "Core and E Antigen Synthesis in Rodent Cells Transformed with Hepatitis B Virus DNA is Associated with Greater than Genome RNAs", Journal of Molecular Biology, 165, pp. 683–699.

*Primary Examiner*—Thomas G. Wiseman
*Assistant Examiner*—John E. Tarcza
*Attorney, Agent, or Firm*—John S. Roberts, Jr.

[57] ABSTRACT

A modified protoplast fusion method and cell line is disclosed that stably transfects human cells with pSV2-derived plasmids at frequencies greater than $10^{-3}$. This procedure makes it possible to test the biological effect of individual genes (i.e., oncogenes and other cellular genes, and viral genes). To demonstrate the utility of this invention, a pSV2gpt+ plasmid constructed to carry a subgenomic fragment of hepatitis B virus (HBV) that contained the core antigen gene (HBc gene) is transfected into human cells. Human cell lines are stably transfected with the HBC+ gene by selecting recipient cells for expression of guanine phosphoribosyl transferase expression; other selective markers, i.e., neomycin resistance, can also be used. Conditions for enhancing the expression of the transfected gene(s) have also been developed. For example, with this gpt+/HBc+ cell line it is shown that growth in serum-free medium or treatment with 5'-azacytidine stimulates the production of the HBV core antigen.

7 Claims, 4 Drawing Figures

PROTOPLAST FUSION METHOD FOR HIGH-FREQUENCY DNA TRANSFECTION IN HUMAN CELLS

UTILITY STATEMENT

The improved fusion method described here for high-frequency transfection of human cells in serum-free growth conditions provides a method for application to general problems in human somatic cell genetics. For example, the ability to stably transfect genes at frequencies greater than $10^{-3}$ in human cell recipients is sufficient to attempt isolation of single-copy genes from genomic libraries linked to selectable markers.

In particular, this method also produces a genetic test for the biological consequences of HBc gene expression separate from the rest of the HBV genome, thus producing a useful screening method to determine the cytopathologic potential of subgenomic fragments of viral DNA before obtaining a stable population of cells carrying the viral gene.

MATERIAL INFORMATION DISCLOSURE

Rassoulzadegan et al, *Nature*, Vol. 295, pp. 257 (1982).

Sandri-Goldin et al, *Mol. and Cell. Biol.*, Vol. 1, p 743 (1981).

Schaffner, *PNAS*, Vol. 77, p 2163 (1980).

These three references disclose methods of protoplast fusion developed for murine, simian, and HeLa cells. The present invention significantly modifies these techniques to obtain high levels of expression, as well as transfection into normal as well as neoplastic human cells.

Dubois et al, *PNAS*, Vol. 77, p 4549 (1980).
Gough et al, *J. Mol. Bio.*, Vol. 162, p 43 (1982).
Hirschman et al, *PNAS*, Vol. 77, p 5507 (1980).
Moriarty et al, *PNAS*, Vol. 78, p 2606 (1981).
Pourcel et al, *J. of Virology*, Vol. 42, p 100 (1982).
Siddiqui, *Mol. and Cell Bio.*, Vol. 3, p 143 (1983).

The above references disclose the present method of transfection, the CaPO$_4$-DNA method. None disclose success with a human cell line, none of these references disclose HBc expression, and none produced a stable cell line capable of carrying only the HBc gene. The Siddiqui reference is closest, detailing the transfection of HBsAg (HB surface antigen) in a simian cell line.

Mulligan et al, *Science*, Vol. 209, p 1422 (1980), discloses transfection using pSV2-derived plasmids in combination with a variety of human genes (none of which are HBV) into SV-40 transformed cells.

STATEMENT OF DEPOSIT

The cell line (GTC2) of this invention has been deposited in the American Type Culture Collection (ATCC) on Oct. 21, 1983. The accession number is CRL 8390. The deposit in the ATCC affords permanence of the deposit in the manner prescribed by the Patent and Trademark Office without restrictions on public access.

BACKGROUND OF THE INVENTION

Figure 1:
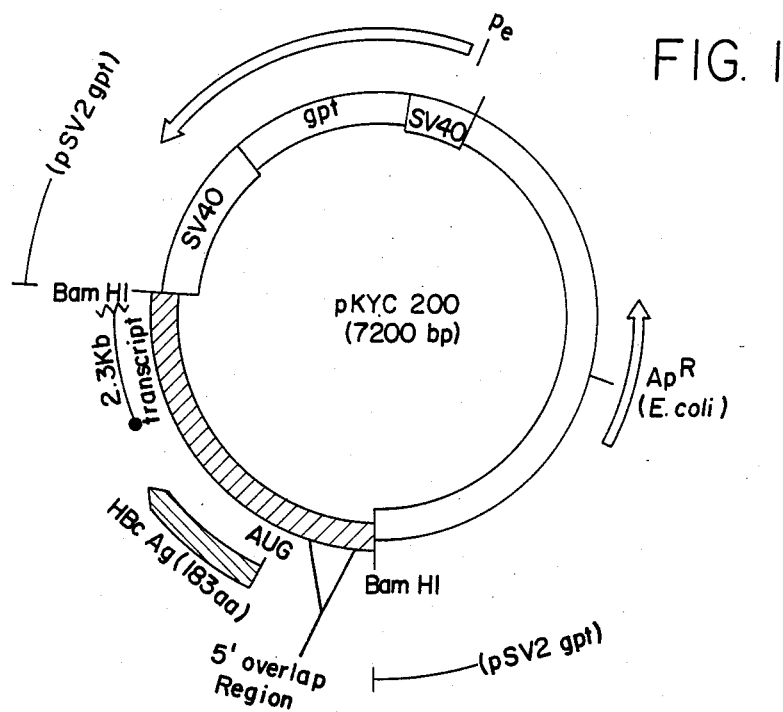
FIG. 1 shows the construction of plasmid pKYC2(K). The HBc gene was localized on an 1850-bp Bam H1 fragment from plasmid pAM6. Plasmid pAM6 contains the HBV genome ligated into pBR322 at the Bam HI site that separates the HBV surface antigen gene (HBs) from its native promoter. The 1850-bp Bam HI fragment released by the Bam HI/Pst I digest of pAM6 DNA was isolated by ligation to pSV2gpt DNA at a 100-fold molar excess of fragment DNA to vector DNA HB10; colonies carrying the pSV2gpt/HBc gene fragment were selected for resistance to ampicillin.

Inventive approaches for high frequency DNA transfection into human cells are needed for a variety of problems in biomedical sciences that are aimed at isolation of human genes, assessment of the pathobiological effects of individual as well as specific combinations of genes, and efficient production of products of transfected genes. As an example of an application of this invention, the pathobiological effects of a viral gene as well as the production of a specific gene product is described. It is not intended that the invention be limited by explication of the specific example.

Hepatitis B virus (HBV), the major cause of viral hepatitis, has been epidemiologically linked to liver cancer. To understand the pathogenesis of HBV infection during acute and chronic disease processes, it is essential to separate various viral genetic elements and to study their biological effects and molecular biology in a model cell systen in vitro. The HBV genome has been isolated on multicopy plasmids and the primary DNA sequence of several subtypes are known in the art [see for example, Burrell et al, Nature, Vol. 279, p 43 (1979); and Sninsky et al, Ibid., p 346]. By adapting the protoplast fusion method of transfection for transfer of pSV2-derived plasmids to a variety of human cells, including cells grown in serum-free media, genes can be transfected into human cells for isolation of genetically stable cell lines at frequencies greater than $10^{-3}$. The human cell lines used are epitheloid cells, primary bronchial epithelial cells, primary lung fibroblasts, mesothelial cells, and lymphoblastoid cells. These cells are specific types from the epithelial, mesynchemial, fibroblast, and hematopoietic classes of cells. With this procedure, the HBV core antigen (HBc) gene is transiently expressed in 70 to 90 percent of recipient cells for 6 to 12 days after transfection and gpt+ (guanine phosphoribosyl transferase positive/HBc+) cells are selected at frequencies greater than $10^3$. The immediate response of the recipient cells to high-frequency transfection provides a genetic test for cytopathologic effects that can be followed by analysis of the factors that regulate HBc gene expression in the stable gpt+/HBc+ population.

Total genomic HBV-DNA has been transfected into a variety of mammalian cell recipients by the $CaPO_4$-DNA method (see the Material Information Disclosure for examples of this method). A subgenomic fragment carrying the HBV surface antigen (HBsAg) gene has been transfected and stably expressed in a COS (Simian) cell line [Siddiqui, Mol. Cell Biol., Vol. 3, p 143 (1983)]. The emphasis of these experiments has been on (i) production of HBsAg, which is immunologically indistinguishable from that produced during HBV infection (Moriarty et al, supra; Dubois et al, supra; and Siddiqui, supra); (ii) the production of viruslike particles resulting in transient cytopathologic effects in HeLa cells (Hirschman et al, supra); and (iii) the study of viral transcripts (Gough et al, supra; Pourcel et al, supra). However, the effect of HBc gene expression is not discernible from these studies, since recircularized HBV genomic DNA is transfected without a selectable marker. Most importantly, these experiments do not result in a stable cell line carrying only the HBc gene for studies of HBc gene expression. Transfer of tandem duplicates of the HBV genome into rat and mouse cells yielded stable cell lines producing detectable levels of HBsAg and HBeAg but not HBV core antigen (HBcAg) (Hirschman et al, supra; Dubois et al, supra). The HBsAg-HBeAg-positive rodent cells did not demonstrate a cytopathologic response to detectable levels of these HBV gene products. Transfection of HeLa cells with recircularized HBV resulted in notable cytopathology when HBsAg, HBcAg, and viruslike particles were observed. The similarity of these effects to those observed with Dane-particle-infected liver hepatocytes suggests that human carcinoma cells may provide effective model recipients for transfection experiments with subgenomic fragments of HBV.

GENERAL DESCRIPTION

High frequency transfection of human cells.

The frequency of stable transfection into NCI H292 cells with pSV2-derived plasmids is $3 \times 10^{-3}$ after selection for the gpt+ or neo+ markers in recipient cells (Table 1 below).

Cells with the gpt+ marker are selected on the basis of their ability to convert xanthine to guanine when grown in medium containing aminopterin and mycophenolic acid; the neo+ (neomycin) marker is selected by growing the cells in medium containing G418-neomycin. The adapted protoplast fusion procedure described here yields substantially higher frequencies of stable transfection into NCI H292 cells than the $CaPO_4$-DNA method. The fraction of recipient cell populations that are selectable for stable transfection of the gpt+ or neo+ genes remains constant when recipient cells are challenged by selection within 72 hours or grown (three to ten divisions) to reach confluence after the transfection procedure. Thus, the biological effects of unstable expression of transferred genes in 70 to 90 percent of the population were observed after transfection, without reducing the gpt+-resistant fraction of the original population of recipient cells. NCI H292 cells were tested for their ability to be transfected by $CaPO_4$-DNA with pSV2gpt+ or neo+ plasmids. Stably resistant cells were unobtainable by the selections used to obtain transfected cells after protoplast fusion (Table 1). The physical methods used here to introduce exogenous DNA are relatively nontoxic. The development of protoplast fusion for human cells grown in serum-free conditions results in a procedure that is applicable to a variety of human cell types (mesynchemial cells, epithelial cells, fibroblast cells, and hematopoietic and lymphoblastoid cells).

TABLE 1

| Recipient Cell Designation | Plasmid | Genotype | Selection gpt+ | Selection neo+ | Frequency of Transfection Protoplast Fusion | Frequency of Transfection $CaPO_4$—DNA (13 mM to 125 mM $Ca^{++}$) |
|---|---|---|---|---|---|---|
| GTC1 | pSV2gpt | gpt+ | + | − | $3.2 \times 10^{-3}$ | $<10^{-5}$ |
| GTC2 | pKYC200 | gpt+, HBc+ | + | − | $3.1 \times 10^{-3}$ | — |
| GTC10 | pSV2neo | neo+ | − | − | $3.4 \times 10^{-3}$ | $<10^{-5}$ |
| TEF 1 | EJras/neo | | − | + | $3.0 \times 10^{-3}$ | |
| TLF 10 | tSV-2 neo | | − | + | $3.0 \times 10^{-3}$ | |
| THL | pSV2 neo | | − | + | Not done | |
| TLM | pSV2 neo | | − | + | Not done | |
| | | | Suspension | Serum | Soft Agar Clonal Growth | |
| TBE 1 | (H1) vHa ras | | + | − | − | $3.0 \times 10^{-3}$ |
| TBE 31 | pAS-1A | | + | + | − | Not done |

TABLE 1-continued

|  | (Adenovirus E1a) |  |  |  |  |
| --- | --- | --- | --- | --- | --- |
| TPE 30 | pSV2 neo | – | + | – | Not done |

TLM = Transfected lung mesothelial
TPE = Transfected prostatic epithelial (sv40)
TBE = Transfected bronchial epithelial
TEF = Transfected esophogial fibroblast
TLF = Transfected lung fibroblast
THL = Transfected hematopoietic lymphoblastoid However, the human cell types tested are sensitive to this fusion procedure when grown in Dulbecco's minimum essential medium (DMEM). Efficient use of the method requires adaptation of these cells to growth in serum-free medium LHC4, RPMl-1640 medium, MCDB 104 or MCDB 151 nitrient media.

Protoplast fusion is a method for directly transferring cloned DNA from bacteria to mammalian cells at high frequency. The principle of this method involves only two steps: the conversion of the bacteria to protoplasts or spheroplasts by digestion of the cell wall with lysozyme and the fusion of the bacterial protoplasts to the animal cells with polyethylene glycol (PEG). Genetic material carried by the bacteria is released into the eukaryotic cells and expressed at high frequency.

Specifically, an *E. coli* strain carrying the appropriate plasmid is grown. Chloroamphenicol is added to amplify the plasmid copy number. After amplification, the bacteria is converted to protoplasts by adding lysozyme. Tissue culture cells are seeded so that a subconfluent cell monolayer is formed. The protoplasts are then pelleted onto the cells. PEG is added to fuse the protoplasts to the cells on the monolayer. The monolayer is then washed, incubated with medium and kanamycin (to prevent the growth of any bacteria which escaped conversion to protoplasts), and then readied for analysis.

Cloned DNA sequences shown to be expressed by a protoplast fusion method are HSV-1 tk gene and HSV-1 sequences within an EcoRI fragment from the long region of the HSV-1 genome [Sandri-Goldin et al, *Mol. Cell. Biol.*, Vol. 1, p 743 (1981)]; SV40 viral DNA [Schaffner, *PNAS*, Vol. 77, p 2163 (1980) and Rassoulzadegan et al, *Nature*, Vol. 295, p 257 (1982)]; polyoma early genes (Rassoulzadegan, Ibid.); a CAD gene from syrian hamster cells [deSaint Vincent et al, *Cell*, Vol. 27, p 267 (1981)]; an *E. coli* gpt gene linked to eukaryotic control signals (deSaint Vincent, Ibid.) and an octopine-type Ti plasmid [Hasezawa et al, *Mol. Gen. Genet.*, Vol. 182, p 206 (1981)]. Since none of these methods permit high frequency transfection into human cells, the present invention significantly modifies the methods of Schaffner, Sandri-Goldin, and Rassoulzadegan mentioned above.

SPECIFIC DESCRIPTION

Plasmid Construction.

To test the biological effects of the HBc gene, a hybrid plasmid is constructed to carry the HBc gene on an 1850-base pair (bp) Bam HI fragment ligated to the Bam HI site of pSV2gpt (pKYC200) (FIG. 1). The HBc+ Bam HI fragment came from plasmid pAM6, which carries the HBV genome on pBR322. Although there is significant variation among subtype sequences, the 1850-bp region carrying the HBc gene is reasonably conserved, and the only complete structural gene on this fragment encodes the HBc gene. The Bam HI site upstream of the HBc gene is mapped just within an open reading frame which is designated X since there is no defined transcript or gene product yet assigned to this region. Consistent with mapping data that locate Bam HI within the X-region open reading frame, sequencing data from the Bam HI fragment of pKYC200 shows neither a complete reading frame or potential fusion reading frame that expresses the X-region of pKYC200. The Bam HI fragment on pKYC200 places the HBc gene in opposite orientation to the SV40 promoter of pSV2 that expresses the gpt+ gene (FIG. 1). This suggests that the HBc gene on pKYC200 is probably expressed from a native promoter between the AUG (adenine, uracil, guanine) triplet at bp 451 and the Bam HI site. High-frequency transfection of pKYC200 into a human epithelial cell line with secretory properties such as NCI H292 provides a genetic test for the biological consequences of HBc gene expression separate from the rest of the HBV genome.

Figure 2:
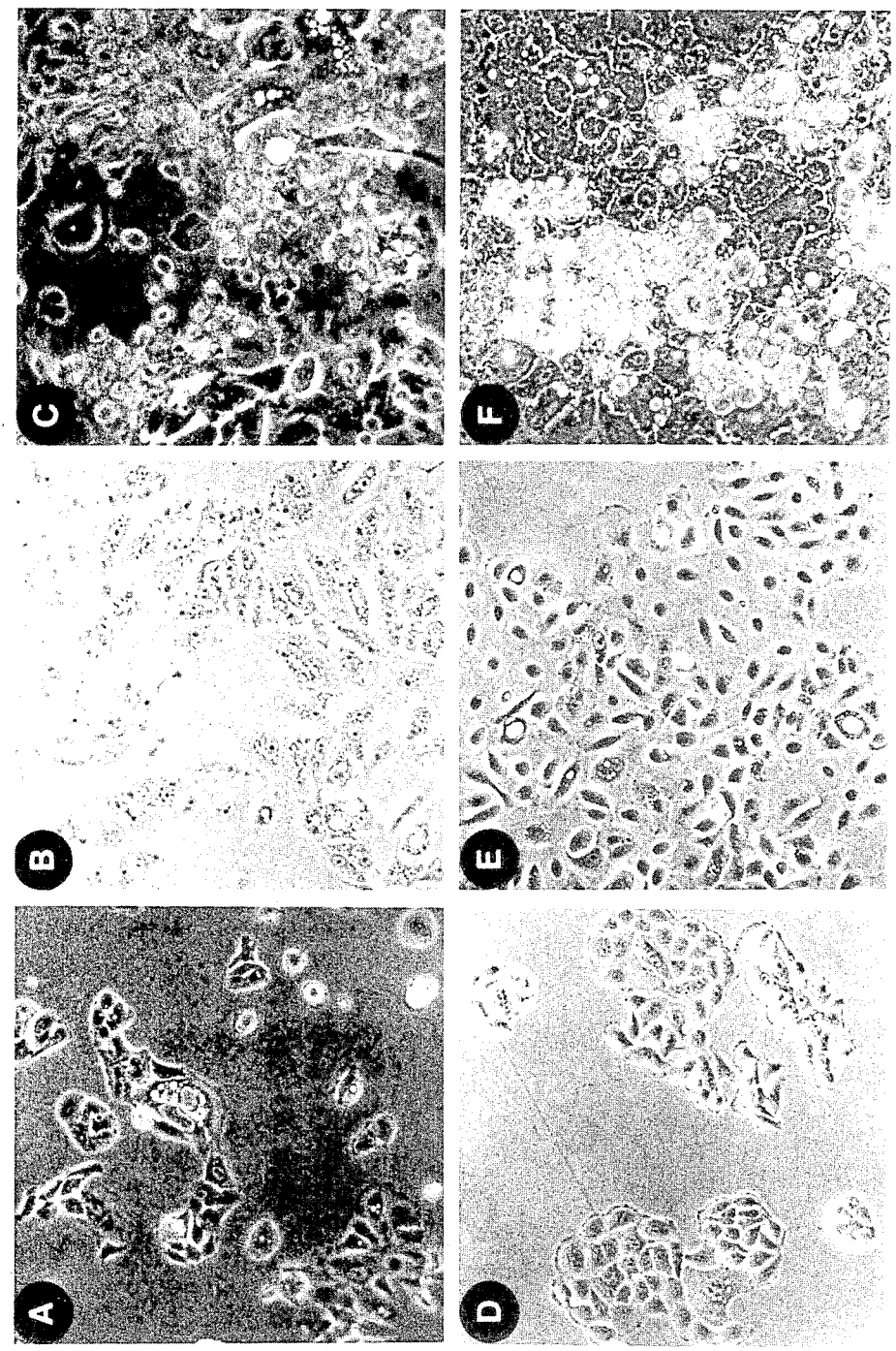
FIG. 2 shows the morphology of human cells expressing the hepatitis B core antigen gene (HBc gene). (A and B) NCI H292 transfected with pKYC200, which carries the 1850-bp Bam HI fragment; from the HBV genome (GTC2) (C and D) NCI H292 transfected with the vector pSVgpt (GTC). These cultures were incubated in LHC4 medium with 5 percent serum (L4-5S) for 3 days (A and C) and 9 days (B and D) prior to selection of the cultures for stable gpt+ recipient cells. (E) The biological crisis that occurs when HBc gene expression reaches its maximum after 5'-azacytidine treatment of GTC2 and two passages in L4-5S medium. (F) The biological crisis of Alexander cells, which occurs at the second passage of these cells in L4-5S medium or following treatment with 5'-azacytidine treatment and growth in MCDB 104 medium containing 2.5 percent FBS (MC-2.5). The cell detachment in (E) and (F) coincides with the peak production of HBc gene product.

After high-frequency transfection of NCI H292 grown in serum-free medium with pSV2gpt (GTC1) or pKYC200 (GTC2) observation of transfected cultures during growth to confluence (6 to 12 days) shows that GTC2 cells become vacuolated and granular within 72 hours; when these cultures approach confluence, cytopathologic changes are apparent in 70 to 90 percent of the population (FIG. 2). However, cells transfected with the vector pSV2gpt remain morphologically indistinguishable from the parent cells (NCI H292) (FIG. 2). The results shown in FIG. 2 A through D indicate that the transient expression of genes during the period immediately following the procedure provides a useful screening method to determine the cytopathologic potential of subgenomic fragments of viral DNA before obtaining a stable population of cells carrying the viral gene by selection for gpt+ expression.

High-frequency transfection into human cells requires significant modification of the protoplast fusion methods developed for murine, simian, and HeLa cells (Schaffner, supra; Sandri-Goldin, et al, supra; and Rassoulzadegan, et al, supra). Protoplasts are prepared by growth of plasmid-carrying derivatives of HB101 *E. coli* in 250 ml of Luria-broth to $2 \times 10^8$ to $5 \times 10^8$ cells per milliliter. Chloramphenicol is added to a final concentration of 200 µg/ml and incubation at 37° C. continued for 18 to 20 hours to amplify the plasmid copy number. After centrifugation, cell pellets are placed on ice and protoplasts are prepared as follows: (i) the pellets are resuspended in 2.5 ml of HBS-20 buffer, (ii) 0.8 ml of freshly mixed lysozyme at 10 mg/ml in HBS-20 is added, and (iii) incubation at room temperature for 15 to 45 minutes is followed by microscopic observation of the conversion of *Escherichia coli* cells to spheroplasts to determine when reactions are complete. After the lysozyme has converted 85 to 90 percent of the cells to spheroplasts, the mixture is placed on ice. 0.4 ml of 1.25M $CaCl_2$ is added to stop the lysozyme and 2.5 ml of 0.25M ethylenediamine tetraacetic acid (EDTA) is added to chelate excess $Ca^{2+}$. This mixture is then diluted by slow addition to 12.5 ml of HBS-9 buffer resulting in a preparation containing approximately $2 \times 10^9$ protoplasts per milliliter.

The fusion procedure is conducted by placing 1.0 ml of 48 percent PEG-1000 fusion reagent and 2.5 ml of protoplast preparation in each 60-mm dish containing $5 \times 10^4$ cells per dish. The cells are selected from the group of human cell lines consisting of epitheloid cells, primary bronchial epithelial cells, primary lung fibroblasts, mesothelial cells, and lymphoblastoid cells. The culture dishes are centrifuged at 850 g for 3 minutes to approximate protoplasts and human cells. The protoplast supernatant is removed and dishes are flooded with 2.5 ml of 48 percent PEG1000 fusion reagent prepared as follows: (i) PEG-1000 (polyethylene glycol) is heated to 42° C.; (ii) 300 to 500 ml of this melted reagent is poured into a large beaker and the pH adjusted to 7.4 with concentrated HCl if needed; (iii) 10 g of Bio-Rad mixed-bed resin AG501-X8(D) is added and the mixture incubated for 4 hours at 40° C.; (iv) the PEG-1000 is collected by filtering the mixture through Whatman paper No. 1, covered by 10 g of unexposed resin into a vacuum flask; (v) the fusion grade PEG is weighed while still warm, and adjusted to a 48 percent solution by weight by the addition of MCDB 151 nutrient medium stock. This PEG-fusion reagent is passed through a 0.22 μm filter for sterilization and stored at $-20°$ C. for as long as 1 year without notable differences in performance. Storage at 4° C. is adequate for several weeks. Preparation methods that involve excessive heating (that is, autoclaving) of PEG and exposure to oxygen generate toxic contaminants that obviate most of the advantages obtained by application of fusion methods to human cell culture experiments involving growth in serum-free media.

Cell and protoplast mixtures are treated with PEG-fusion reagent for 45 to 60 seconds, the mixture is removed, and the culture dishes are carefully washed three to five times with MCDB 151 medium to remove most of the residual PEG. Washed cells are covered with LHC4 growth medium and placed in the incubator, the medium is changed at 1-hour intervals for the next 3 hours. The LHC4 culture medium is subsequently changed each morning for the next 3 days. Within 48 to 72 hours after the procedure, transfected cells can be handled normally, for example, trypsinized for passage. "Stable" transfectants for this study are defined as those populations that maintain the selected marker in 80 to 90 percent of the cells after growth for a minimum of ten divisions without selection.

Hybridization Analysis of GTC2 Cells.

Figure 3:
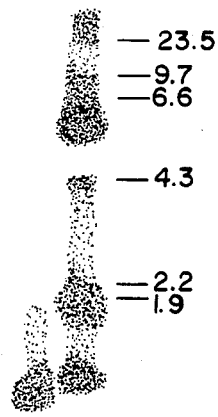
FIG. 3 is a Southern blot analysis of nuclear DNA from gpt+ GTC2 cultures. Nuclei were isolated from gpt+/HBc GTC2 and NCI H292 cells and high-molecular-weight DNA was purified for restriction and hybridization with $^{32}$-labeled pAM6 DNA. The HBV-probe revealed the presence of HBV-sequences by hybridization to several bands ranging in size from 0.9 to 10.0 kbp. Lane 1 is Msp I/Bam HI and lane 2, Hpa II/Bam HI digests of parental DNA (NCI H292). Lane 3 is Msp I/Bam HI and lane 4, Hpa II/Bam HI digests of GTC 2 DNA.

NCI H292 cells stably carrying the pKYC200 plasmid (GTC2) and constructed by the above process were isolated by selection for the expression of the gpt+ gene (Table 1). The transfected genes have remained stably integrated after more than 30 passages of GTC2 cells in RPM1-1640 medium containing 10 percent fetal bovine serum (FBS) (HUT medium). The gpt+ GTC2 cell line was used to test for the physical presence of the HBc gene and to ascertain the factors regulating the expression of the HBc gene. To detect the physical presence of pKYC200 sequences in GTC2 cells, high-molecular-weight DNA was isolated from cell nuclei for Southern blot analysis. GTC2 DNA was probed with pAM6 DNA after Bam HI/Hpa II or Bam HI/Msp I restriction enzyme digests to detect the presence of pKCY200 sequences in nuclear DNA. The pAM6 probe detected sequences between 0.9 and 10 kbp, and no hybridization to NCI H292 DNA was observed (FIG. 3). Hybridization analysis indicates that nuclear DNA from GTC2 cells contains sequences from pKYC200 after transfection and selection for the gpt+ marker and that such cell lines may be mapped for gene-specific response to 5'-azacytidine treatment.

EXAMPLE

Measurement of HBcAg in GTC2 and Alexander Cells

GTC2 cells were tested for the presence of a functional HBc gene by indirect immunofluorescence assay with an antibody to HBcAg (anti-HBcAg). Robinson et al have reported that a hepatocellular carcinoma cell line that has carried the HBV genome since its isolation (Alexander cells) expresses the HBcAg after 5'-azacytidine treatment (W. S. Robinson et al, personal communication). Therefore, GTC2 cells were treated with 5'-azacytidine before conducting immunofluorescence assays. Greater than 90 percent of GTC2 cells expressed the HBcAg after treatment with 5'-azacytidine and growth in LHC-4 with 5 percent FBS (L4-5S) medium. Alexander cells also became positive for expression of HBcAg after 5'-azacytidine treatment.

Figure 4:
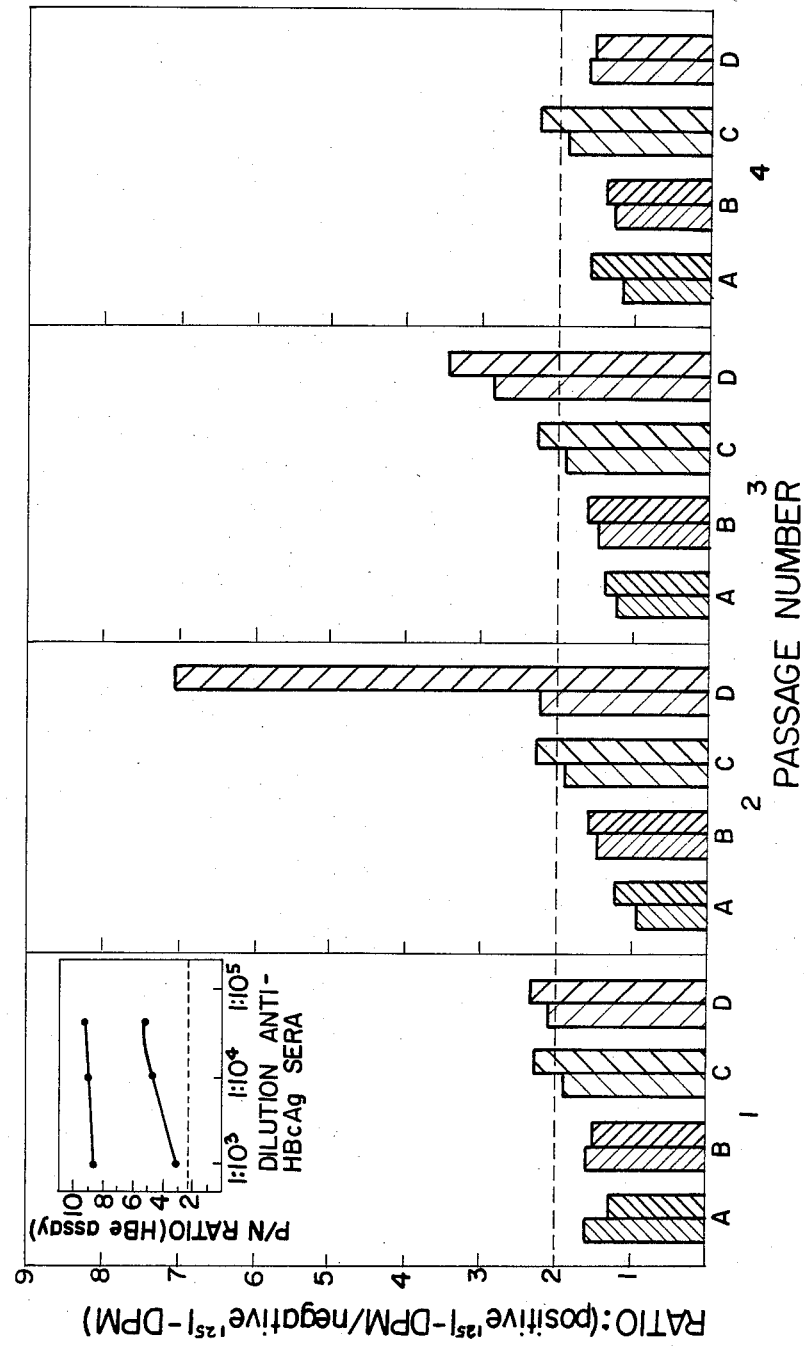
In FIG. 4, to quantitatively compare growth conditions that affect the cytopathologic response of GTC2 cells and HBV-carrying Alexander cells for the production of HBcAg, the commercially available HBc radioimmunoassay diagnostic kit (Abbott) was adapted for application to the measurement of HBcAg in extracts from cells grown in culture. The inset shows the response of the HBc assay kit positive control to the human anti-HBcAg between dilution of 1:1000 and 1:80,000 (open triangles). The observation of no blocking activity for human anti-HBcAg indicates a high degree of specificity for the HBcAg. The GTC2 extract (closed circles) yields a P/N ratio of 5.0; however, the reaction of the extract with human anti-HBcAg yielded blocking of the kit response to P/N ratios between 2.8 and 5.0. The P/N ratios measured for cell extracts after growth in HUT medium are shown for each condition tested by less dense marking of the bars. The values reached by cell extracts after growth in L4$^{-3}$. medium are indicated by heavily marked bars. The bars are labeled as follows: A, measurements of GTC1 cells (pSV2gpt+) grown in HUT or L4-5S medium; B, GTC1 cell extracts after 5'-azacytidine treatment; C, GTC2 cell extracts (pKYC200 gpt+/HBc+); D, GTC2 cells after 5'-azacytidine treatment.

To quantitate the level of HBcAg expressed during various growth conditions, the HBeAg assay kit (Abbott) was adapted for use with cell extracts (FIG. 4). To test the applicability of this kit for HBcAg measurements in cellular extracts, a linear positive response to diluted extracts was determined, in the range used for HBc gene product assay. The anti-HBcAg was tested for cross-reactivity to HBeAg using the positive HBeAg control provided with the assay kit (insert). The anti-HBcAg preparation did not cross-react with HBeAg. The linear blocking response by anti-HBcAg in the 2.8- to 5-fold range of the positive to negative (P/N) ratio indicates that the HBe assay kit can be used to quantitatively compare cell extracts for the production of HBc gene product (FIG. 4, insert). The dashed line indicates the P/N ratio at which the measurement reaches 99.4 percent detection confidence (Abbott). Variations of ±0.05 in the P/N ratio were found between duplicate measurements of HBcAg when cell extracts were substituted for serum samples and the reaction mixtures formulated as described by the manufacturer (Abbott). The level of HBc gene product reached a maximum when GTC2 cells were passaged in L4-5S after treatment with 5'-azacytidine (FIG. 4).

LHC-4 medium is a serum-free nutrient medium, developed for primary human epithelial cell culture that causes terminal differentiation of epithelial cells when serum is included. However, when serum is deleted from L4-5S, GTC2 and Alexander cells are stimulated to produce the same level of HBcAg, indicating that one or more of the growth factors and hormones included in LHC-4 medium is positively regulating HBc gene expression. The most notable effect of including 5 percent serum in LHC-4 medium for these experiments is an increase in the growth rate for the GTC2 and Alexander cells. At the second passage of 5'-azacytidine-treated GTC2 cells in L4-5S medium, the maximum level of HBc gene product (HBcAg) coincided with a cytopathologic response and most of the cells detached (FIG. 2E, FIG. 4). However, some cells (approximately $10^{-4}$) remained attached and grew to confluence (GTC2-1) in L4-5S medium, and the level of HBcAg dropped below detection limits at cell passage 4 (FIG. 4).

Karyotype analysis of GTC1, GTC2, GTC2-1 and NCI H292 showed that these cells carry the same marker chromosomes, indicating a parental relationship to NCI H292. The basal level of expression of HBcAg is maintained by GTC2 cells grown in L4-5S medium without 5'-azacytidine treatment (FIG. 4). Since the anti-HBcAg does not cross-react with HBeAg, and since the antibody preparation blocks 80 to 90 percent of the activity of the GTC2 extract (FIG. 4 inset), most of HBc gene product measured in GTC2 extracts was HBcAg.

The relative response of Alexander cells was determined for the production of HBcAg after growth in L4-5S medium or 5'-azacytidine treatment and growth in MCDB 104 medium with 2.5 percent FBS (MC-2.5). Either of these conditions stimulated the production of HBcAg to P/N ratios of 3.5 to 3.8 and a cytopathologic response for Alexander cell cultures (FIG. 2F). Alexander cells initially increased their growth rate when passaged into L4-5S medium to from 0.8 to 1.0 population doublings per day (PD/day). However, at the second cell passage in this medium, PD/day decreased to 0.65, the cells produced HBcAg at P/N ratios of 3.5 to 3.8, and then they detached in a manner very similar to the response observed for GTC2 cells after 5'-azacytidine treatment and growth in L4-5S medium (FIGS. 2 and 4). A similar response was obtained for Alexander cell cultures after treatment with 5'-azacytidine and growth of these cells in MC-2.5. Although Alexander cell extracts did not exceed P/N ratios of 3.5 to 3.8, the morphologic response was similar to that observed for GTC2 cells carrying only the HBc gene (FIG. 2). Treatment with 5'-azacytidine deregulates genes controlled by cytosine methylation and serum-free medium includes hormones and growth factors not present in HUT medium. The cytopathologic response of Alexander cells to conditions that increase the expression of HBc gene product, and the similarity of this response to that of GTC2 cells, indicate that HBc gene regulation and the cytopathologic response of GTC2 and Alexander cells are the same.

In step fashion, the following describes the preferred protocol:

Reagents

A. PEG-Fusion Reagent

1. Polyethylene glycol 1000 (PEG1000) is melted by heating to 40°–42° C.

2. After melting, pour 300–500 ml of melted PEG1000 into an 800 ml beaker. Test pH and adjust to pH 7.4 if needed. Add 10 grams of Dowex mixed bed resin, and mix in a 37° C. waterbath as a PEG/resin slurry for 4 hours.

3. Slowly filter the PEG/resin slurry through the fresh resin and collect the "Fusion-Grade PEG" in the vacuum flask. This will remove toxic products from the PEG that accumulate during heating and/or storage at room temperature. Most human cells are particularly sensitive to these toxic components.

4. Place a 1 liter beaker on the balance and weigh the Fusion-Grade PEG and prepare the PEG-Fusion Reagent by addition of appropriate diluent (i.e., MCDB151 nutrient medium) to yield a 48% w/w solution.

5. Filter sterilize the PEG-Fusion Reagent through 0.22u filter and store at −20° C. in 100–200 ml aliquots. This is stable for at least 1 year and may be stored for several weeks at 4° C. without changing the experimental performance. Do not heat the PEG-reagent being used for human cell fusion experiments.

B. Transfection Buffers

1. Transfection HBS (HEPES Buffered Saline): HEPES 20 mM/Dextrose 6 mM/KCl 0.7 mM/NaCl 5 mM/Na$_2$HPO$_4$ 137 mM pH 7.1 (no indicator dye). Filter sterilized.

2. HBS-20: Transfection HBS with 20% sucrose.

3. HBS-9: Transfection HBS with 9% sucrose.

Protocol

A. Protoplast Preparation

1. Prepare 20 ml Luria-broth overnight cultures with the appropriate antibiotic to select for *E. coli* culture carrying the plasmid to be transfected.

2. The following morning dilute the overnight culture to yield a 250 ml L-broth culture at approximately $2 \times 10^7$ cells/ml. Incubate at 37° C. until cell density reaches $2 \times 10^8$ cells/ml and add chloramphenicol to 200 ug/ml final concentration. Continue incubation overnight.

3. Centrifuge the culture at 4000 g for 15 minutes to pellet the cells. Resuspend cell pellet in 2.5 ml of HBS-20. Add 0.8 ml of freshly prepared lysozyme: 10 mg/ml in HBS-20 filter sterilized. Incubate at room temperature for 15–45 minutes and determine the completion of reaction by observing the formation of protoplasts in the microscope.

4. After the lysozyme reaction is 80–90% complete add 0.4 ml of 1.25M CaCl$_2$ to terminate the lysozyme reaction. Mix gently, add 2.0 ml 0.25M EDTA to chelate excess Ca$^{++}$.

5. Mix. Dilute the protoplast preparation by addition of 10 ml HBS-9. This will yield enough protoplast preparation to treat six 60 mm dishes of human cell cultures at $2–10 \times 10^5$ cells/dish. In most cases the protoplast may be more dilute within an approximate range of ⅓ without changing transfection efficiency.

B. Protoplast fusion to human cells.

1. Remove medium from a 50–80% confluent 60 mm culture dish.

2. Add 1.5 ml PEG-fusion reagent. Immediately add 2.5 ml dilute protoplast preparation. Place the dishes on a centrifuge platform.

3. Centrifuge at 850 g for 3 minutes to approximate protoplast and human cells.

4. Aspirate to remove excess protoplast/PEG-fusion reagent mixture.

5. Add 1.5 ml of fresh 48% PEG-fusion reagent and treat for 45–60 seconds.

6. Remove PEG-fusion reagent by adding 5 ml volumes of MCDB 151 medium until appropriate removal of excess material is obtained (3–5X).

7. Add fresh nutrient medium and place in the incubator. Repeat at one interval for 2–3 hours and change medium daily for the first 3 days.

8. After 72 hours the cultures may be routinely passaged or maintained until confluence then passaged for selection of transfected marker genes.

We claim:

1. A process for stably transfecting a variety of human cell types with recombinant plasmids capable of replicating in *E. coli* comprising producing a stable protoplast containing a recombinant plasmid;
   fusing said stable protoplast with human cells in the presence of fusion grade PEG reagent previously treated with an ion exchange resin;
   removing said PEG reagent by dilution;
   and incubating an analyzing for said recombinant plasmid.

2. A process for stably transfecting a variety of human cell types with recombinant plasmids capable of replicating in *E. coli* consisting essentially of mixing lysozyme with *E. coli,* said *E. coli* containing a recombinant plasmid until stable protoplasts are formed;

diluting said protoplast preparation with fusion grade PEG reagent previously treated with an ion exchange resin before adding the mixture to human cells;

centrifuging and aspirating to remove excess protoplast/PEG reagent mixture;

adding a second treatment of said fusion grade PEG reagent; removing said fusion grade PEG reagent by dilution; incubating and analyzing for recombinant plasmid.

3. A process for stably transfecting a variety of human cell types with recombinant plasmids capable of replicating in *E. coli* consisting essentially of mixing lysozyme with *E. coli,* said *E, coli* containing a recombinant plasmid until stable protoplasts are formed;

adding CaCl$_2$ followed EDTA to form a stable protoplast preparation;

diluting said protoplast preparation with fusion grade PEG reagent previously treated with an ion exchange resin before adding the mixture to human cells;

centrifuging and aspirating to remove excess protoplast/PEG reagent mixture;

adding a second treatment of said fusion grade PEG reagent for 45–60 seconds;

removing said fusion grade PEG reagent by adding culture medium;

incubating and analyzing for recombinant plasmid.

4. The process of claim 3 wherein the human cells are selected from the group consisting of epitheloid cells, primary bronchial epithelial cells, primary lung fibroblasts, mesothelial cells, and lymphoblastoid cells.

5. The process of claim 3 wherein the human cells are selected from the group consisting of epithelial cells, mesynchemial cells, fibroblast cells, and hematopoietic cells.

6. Cell line GTC2 deposited in the American Type Culture Collection under ascession #CRL8390 said cell line characterized by producing high levels of HBcAg, said human cell lines have been produced by a protoplast fusion method.

7. A protoplast fusion process providing a method to efficiently transfect into human cells segments of DNA linked to plasmids that replicate in *E. coli* consisting essentially of fusing a human cell to an *E. coli* protoplast, with fusion grade PEG-1000 reagent previously treated with an ion exchange resin, said *E. coli* protoplast consisting of *E. coli* bacteria containing pKYC200 recombinant plasmid, said pKYC200 recombinant plasmid consisting of the HBc+ Bam HI fragment of plasmid pAM6 ligated to the Bam HI site of pSV2gpt.

* * * * *